United States Patent
Kajiyama

(10) Patent No.: US 6,376,208 B1
(45) Date of Patent: Apr. 23, 2002

(54) METHOD AND REAGENT FOR QUANTITATING D-CYSTEINE

(75) Inventor: Naoki Kajiyama, Chiba (JP)

(73) Assignee: Kikkoman Corporation, Noda (JP)

( * ) Notice: Subject to any disclaimer, the term of this patent is extended or adjusted under 35 U.S.C. 154(b) by 0 days.

(21) Appl. No.: 09/534,283

(22) Filed: Mar. 24, 2000

(30) Foreign Application Priority Data

Mar. 24, 1999 (JP) ............................................. 11-079691

(51) Int. Cl.[7] ............................. C12Q 1/66; C12Q 1/37
(52) U.S. Cl. ............................... 435/8; 435/24; 435/23
(58) Field of Search ................................. 435/8, 23, 24

(56) References Cited

U.S. PATENT DOCUMENTS 5,035,999 A * 7/1991 Geiger et al. .................. 435/23

OTHER PUBLICATIONS

Y. Toya et al., "A Convenient Synthetic Method of 2–Cyano–6–methoxybenzothiazole,–A Key Intermediate for the Synthesis of Firefly Luciferin," Bull. Chem. SocJpn., vol. 65, No. 2, pp. 392–395 (1992).

* cited by examiner .

*Primary Examiner*—Louise N. Leary
(74) *Attorney, Agent, or Firm*—Finnegan, Henderson, Farabow, Garrett & Dunner, L.L.P.

(57) ABSTRACT

The present invention relates to a method and a reagent for quantitating D-cysteine in a convenient and highly-sensitive manner.

The present invention provides a method for quantitating D-cysteine in a sample, comprising the steps of: (a) reacting D-cysteine with a D-luciferin precursor to produce D-luciferin or a D-luciferin derivative; and (b) quantitating D-cysteine by determining the level of the produced D-luciferin or D-luciferin derivative. The D-luciferin precursor may be 2-cyano-6-hydroxybenzothiazole or 2-cyano-6-O-β-D-galactosylbenzothiazole.

The present invention also provides a reagent for quantitating D-cysteine, which comprises the D-luciferine precursor.

2 Claims, 1 Drawing Sheet

METHOD AND REAGENT FOR QUANTITATING D-CYSTEINE

FIELD OF THE INVENTION

The present invention relates to a method and a reagent for quantitating D-cysteine.

BACKGROUND OF THE INVENTION

Almost all amino acids existing in organisms have been considered to be L-amino acids until recently when a high amount of D-amino acids were found in higher animals including mammals. Since there is a growing interest in sources and roles of the D-amino acids in the fields of biotechnology, clinical test, medical science and the like, it has become very important to establish a method for quantitating D-amino acids in an easy, rapid and highly-sensitive manner.

D-cysteine is one kind of D-amino acids. Conventionally, D-cysteine in a sample was quantitated, for example, by high performance liquid chromatography.

The present invention aims at providing a method and a reagent for quantitating D-cysteine in a convenient and highly-sensitive manner.

We achieved the present invention by finding that D-cysteine can be quantitated by, first, reacting D-cysteine and a D-luciferin precursor, and then reacting D-luciferin produced by the first reaction with luciferase.

SUMMARY OF THE INVENTION

The present invention relates to a method for quantitating D-cysteine, and provides the following (i) to (v):

(i) A method for quantitating D-cysteine in a sample, comprising the steps of:
  (a) reacting D-cysteine with a D-luciferin precursor to produce D-luciferin or a derivative thereof; and
  (b) quantitating D-cysteine by determining the level of the produced D-luciferin or D-luciferin derivative.
(ii) A method for quantitating D-cysteine according to (i) above, wherein the step of determining the level of the produced D-luciferin or D-luciferin derivative is carried out by determining a level of luminescence generated upon reacting D-luciferin or a derivative thereof with a bioluminescent reagent.
(iii) A method for quantitating D-cysteine according to (i) above, wherein the D-luciferine precursor is 2-cyano-6-hydroxybenzothiazole or 2-cyano-6-O-β-D-galactosylbenzothiazole.
(iv) A method for quantitating D-cysteine according to (iii) above, wherein the step of determining the level of the produced D-luciferin or D-luciferin derivative is carried out by determining a level of luminescence generated upon reacting D-luciferin or a derivative thereof with a bioluminescent reagent.
(v) A method for quantitating D-cysteine, comprising the steps of:
  (a) reacting D-cysteine with 2-cyano-6-hydroxybenzothiazole to produce D-luciferin; and
  (b) calculating a D-cysteine level by determining a level of luminescent generated upon reacting the produced D-luciferin with luciferase, ATP and magnesium ion.

The present invention also relates to a reagent for quantitating D-cysteine, and provides the following (vi) and (vii):

(vi) A reagent for quantitating D-cysteine, comprising a D-luciferin precursor.
(vii) A reagent for quantitating D-cysteine, comprising a D-luciferin precursor and a bioluminescent reagent.

This specification includes all or part of the contents as disclosed in the specification of Japanese Patent Application No. 11-79691, which is a priority document of the present application.

DETAILED DESCRIPTION OF THE INVENTION

Figure 1:
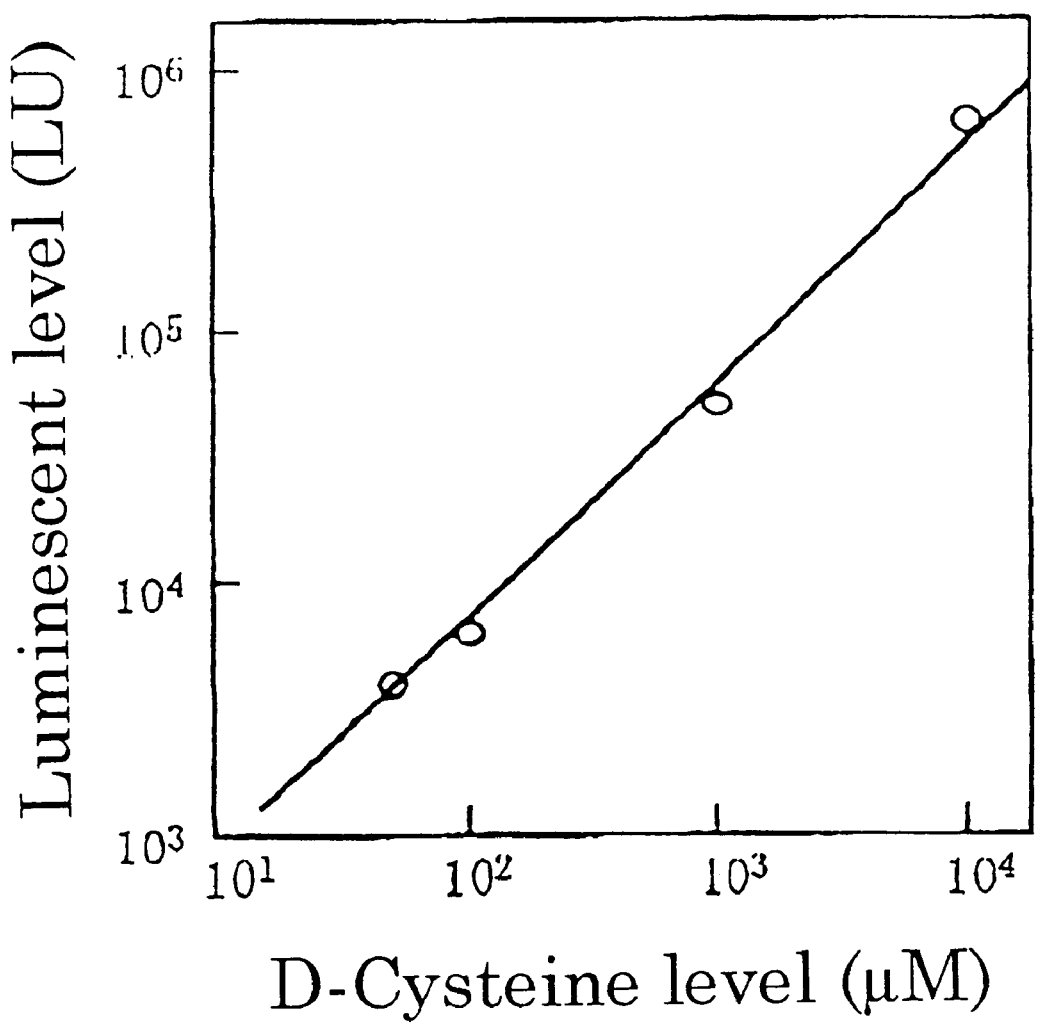
FIG. 1 is a graph showing the relationship between the D-cysteine level and the luminescent level in a sample according to Example.

1. Method for Quantitating D-cysteine in Sample

Method for quantitating D-cysteine in sample according to the present invention includes the following Steps 1 and 2.

(i) Step 1

In Step 1, D-cysteine is reacted with a D-luciferin precursor to produce D-luciferin or a D-luciferin derivative.

Herein, the term "D-luciferin precursor" refers to a compound which is capable of producing D-luciferin or a D-luciferin derivative by reacting with D-cysteine. The D-luciferin precursor may be, for example, 2-cyano-6-hydroxybenzothiazole. The reaction between D-cysteine and 2-cyano-6-hydroxybenzothiazole is represented as follows:

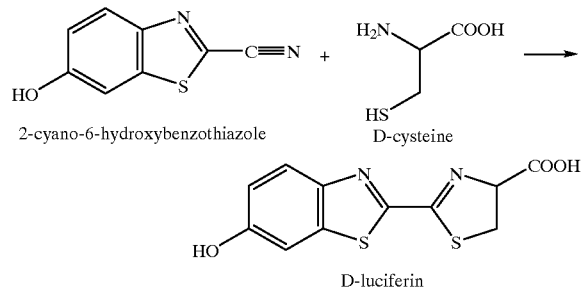

The term "D-luciferin derivative" as used herein refers to a compound having a substantial structure of D-luciferin, which may vary depending on the type of the D-cysteine derivative and the types of other reagents added to the reaction system. For example, the D-luciferin derivative may be salt, ester or glycoside of D-luciferin.

Examples of D-luciferin salts include salts with alkali metals (Na, K, Li, etc.) or alkali earth metals (Ca, Ba, Mg, etc.), and ammonium salts. Examples of D-luciferin esters include esters with alcohol, monosaccharide, disaccharide and oligosaccharide.

Examples of glycosides include glycosides with monosaccharide, disaccharide and oligosaccharide. Specifically, luciferin-β-D-galactoside, luciferin-β-D-glucoside and the like are exemplified. Luciferin-β-D-galactoside produces D-luciferin by reacting with sugar hydrolase such as β-galactosidase. Where the D-luciferin derivative is luciferin-β-D-galactoside, a D-luciferin precursor of the invention may be 2-cyano-6-O-β-D-galactosylbenzothiazole.

The samples to which the present invention may be applied include, but not limited to, those expected to contain D-cysteine, such as foods, drinks, medicines, cosmetics, seawater, river water, industrial water, sewage, soil, biological materials (e.g., urine, feces, blood, sputum, pus, tissues such as skin, organ and hair, and extracts from an organism) and microorganism cultures. These samples may be suspended in an appropriate solvent (e.g., distilled water, physiological saline, phosphate buffer, Tris buffer, sodium acetate buffer) to be used in the form of solution. A sample containing a solid content may be suspended in an appropriate solvent (e.g., distilled water, physiological saline, phosphate buffer, Tris buffer, sodium acetate buffer) or homogenized with a mixer or the like to be used similarly to a solution.

Although any methods may be employed to carry out Step 1, a convenient method is to contact the sample with a solution containing D-luciferin precursor. The solution containing the D-luciferin precursor may contain, other than D-luciferin precursor, components generally used for promoting reaction and preserving the reagent, such as a buffer, a chelating agent, salt, surfactant and the like. An exemplary solution is a reagent for quantitating D-cysteine described below.

The conditions for contacting the sample with the solution containing D-luciferin precursor (e.g., mixing ratio, contact temperature, contact time and pH) are suitably selected depending on the type of the sample or the D-luciferin precursor, the form of the sample, and the like.

For example, 2-cyano-6-hydroxybenzothiazole is dissolved in an organic solvent when used as the D-luciferin precursor. The prepared D-luciferin precursor solution is added to the sample to react with D-cysteine in the sample. The reaction proceeds non-enzymatically. The time and the temperature for the reaction are not limited. For example, the reaction may take place at 20° C. to 40° C. for 1 to 20 minutes.

When an organic solvent containing a D-luciferin precursor cannot be dissolved in an aqueous sample, an organic solvent phase and an aqueous phase are mixed to react while being agitated such that both phases are sufficiently contacted with each other.

(ii) Step 2

In Step 2, the level of the produced D-luciferin or the derivative thereof is determined so as to quantitate D-cysteine. The level of D-luciferin is determined, for example, by measuring the level of luminescence generated upon reacting D-luciferin with a bioluminescent reagent.

The term "bioluminescence" as used herein refers to a luminescent reaction between a luminescent substrate luciferin and an enzyme luciferase. With an insect system (e.g., *Luciola cruciata, Luciola lateralis* or *Pyrophorus plagiophthalamus*), luminescence is generated via the reaction between D-luciferin and the insect luciferase in the presence of ATP and magnesium ion.

Where an insect system is used in Step 2, a bioluminescent reagent containing insect luciferase, ATP and magnesium ion may be allowed to contact with the D-luciferin or the derivative thereof produced in Step 1 in the form of a solution. Then, the luminescent level generated thereby is measured to determine the D-luciferin level. The luminescent level may be measured with a luminometer such as Lumitesters C-100, K-100, K200, K210 (Kikkoman Corp.), Luminescence Reader BLR-201 (Aloka) or Lumat LB9501 (Berthold).

In order to calculate D-cysteine level from the luminescent level, a calibration curve is preferably prepared beforehand. The calibration curve is prepared as follows. First, the fixed amount of commercially available D-cysteine is dissolved in water or in a buffer and appropriately diluted to obtain a D-cysteine solution. Then, a D-luciferin precursor such as 2-cyano-6-hydroxybenzothiazole is added to the D-cysteine solution to produce D-luciferin, which is, in turn, reacted with a bioluminescent reagent. The level of luminescence generated upon the reaction is measured, thereby obtaining the calibration curve.

Accordingly, the D-cysteine in the sample can be quantitated. The method of the invention is useful not only for quantitating D-cysteine existing in a free form but also for quantitating a D-cysteine derivative. The term "D-cysteine derivative" as used herein refers to a compound capable of producing D-luciferin or a D-luciferin derivative by reacting with a D-luciferin precursor. For example, the D-cysteine derivative may be salt, ester, glycoside or amide of D-luciferin or a polypeptide including D-cysteine residue.

Examples of D-cysteine salts include salts with alkali metals (Na, K, Li, etc.) or alkali earth metals (Ca, Ba, Mg, etc.), ammonium salts, phosphate, sulfate, hydrochloride and salts with carboxylic acid. Examples of D-luciferin esters include esters with alcohol, monosaccharide, disaccharide and oligosaccharide. Examples of glycoside include glycosides with monosaccharide, disaccharide and oligosaccharide. An example of amide includes an amide of carboxylic acid.

The concept of the term "D-cysteine" of the invention includes D-cysteine derivatives.

For example, in the case where a D-luciferin precursor is 2-cyano-6-hydroxybenzothiazole, the carboxyl group of D-cysteine may be modified in any way as long as Step 2 is successfully carried out. In this case, a D-cysteine derivative may be, for example, a polypeptide chain having a D-cysteine residue at its N-terminus. Such a polypeptide chain may react with 2-cyano-6-hydroxybenzothiazole to produce a D-luciferin derivative (a compound in which the carboxyl group of D-luciferin is linked to the polypeptide chain via peptide bond). The D-luciferin derivative may be determined after liberating D-luciferin with protease or the like.

Since a D-cysteine derivative can be determined as well, the present invention is particularly useful as a method for quantitating D-cysteine in a biopolymer (such as a protein) constituting an organism, or D-cysteine in an tissue (e.g., an organ, skin or hair) of an organism.

2. Reagent for Quantitating D-cysteine

A reagent for quantitating D-cysteine of the invention comprises a D-luciferin precursor. Examples of the D-luciferin precursor include, but not limited to, 2-cyano-6-hydroxybenzothiazole and 2-cyano-6-O-β-D-galactosylbenzothiazole. The quantitating reagent may contain, other than the D-luciferin precursor, components generally used for promoting reaction and preserving the reagent, such as a buffer, a chelating agent, salt, a surfactant and the like. The reagent may be in the form of a solution, or in a frozen or dried condition, preferably in the form that allows reaction with D-cysteine in a solution state.

The quantitating reagent of the invention may contain a D-luciferin precursor and a bioluminescent reagent. In this case, the D-luciferin precursor and the bioluminescent reagent may be stored separately or together as a mixture.

Use of the quantitating reagent of the invention enables to properly carry out the above-described method for quantitating D-cysteine.

The present invention may be carried out as follows where 2-cyano-6-hydroxybenzothiazole solution is used as a reagent for quantitating D-cysteine, and where a bioluminescent reagent containing firefly luciferase, ATP and magnesium ion is used for determining the level of the produced D-luciferin.

First, in Step 1, a reagent for quantitating D-cysteine is added to a sample. If D-cysteine is present in the sample, it reacts with 2-cyano-6-hydroxybenzothiazole to produce D-luciferin. Then, in Step 2, a bioluminescent reagent is added to the sample to measure the generated luminescent level with a luminometer. Finally, the D-cysteine level in the sample is calculated from the luminescent level based on the calibration curve prepared beforehand.

EXAMPLE

Hereinafter, the present invention will be described in more details by way of an example. It should be noted that the present invention is not limited by this example. In the following example, a D-cysteine solution of a known concentration was used as a sample, and 2-cyano-6-hydroxybenzothiazole solution was used as a reagent for quantitating D-cysteine. The level of the produced D-luciferin was determined by using a bioluminescent reagent containing firefly luciferase, ATP and magnesium ion.

Synthesis of 2-cyano-6-hydroxybenzothiazole

A mixture of 0.48 g of 2-cyano-6-methoxybenzothiazole (Sigma) and 1.0 g of pyridinium chloride (Wako Pure Chemical Industries, Ltd.) was placed into a metal tube filled with nitrogen gas and sealed. The tube was heated at 200° C. for 45 minutes. Thereafter, a saturated aqueous solution of sodium hydrogencarbonate (Wako Pure Chemical Industries, Ltd.) was added to the reaction to adjust pH to 7.0, and the deposited precipitate was separated with a filter paper. The precipitate was washed with water and dried under reduced pressure. The resultant powder was dissolved in 1 ml of dichloromethane and loaded into a silica gel column to perform column chromatography using dichloromethane as an eluate. The 2-cyano-6-hydroxybenzothiazole fraction was collected and dried with an evaporator.

As a result, about 0.4 g of 2-cyano-6-hydroxybenzothiazole was obtained.

Preparation of Reagent

A reagent containing the followings was prepared in order to quantitate D-cysteine.

(i) Reagent for quantitating D-cysteine (2-cyano-6-hydroxybenzothiazole solution):
  One mg of 2-cyano-6-hydroxybenzothiazole dissolved in 1 ml of ethanol.
(ii) 0.2 M potassium carbonate solution
(iii) Buffer for determining activity:
  50 mM HEPES buffer (pH 7.8)
  0.3 M $MgSO_4$
(iv) Luciferase/ATP solution:
  50 mM HEPES buffer (pH 7.8)
  40 mM ATP
  10 mg/ml *Luciola cruciata* luciferase (v) sample (D-cysteine solution):
  D-cysteine (Wako Pure Chemical Industries, Ltd.) was dissolved in pure water to prepare D-cysteine solutions of varied concentrations (50 $\mu$M, 100 $\mu$M, 1 mM, 10 mM).

Quantitation of D-cysteine

To 10 $\mu$l of 2-cyano-6-hydroxybenzothiazole solution, 80 $\mu$l of 0.2 M potassium carbonate solution and 10 $\mu$l of D-cysteine solution were added to react at 30° C. for 10 minutes. To 10 $\mu$l of the reaction solution, 90 $\mu$l of a buffer for activity, and further 100 $\mu$l of luciferase/ATP added to determine the luminescent level with Luminescence Reader (Aloka) for 20 seconds. If necessary, the reaction solution was diluted with the buffer for determining activity before the determination. Results are shown in FIG. 1.

FIG. 1 is a graph wherein the horizontal axis represent the D-cysteine level in the sample and the vertical axis represents the luminescent level determined with Luminescence Reader.

It can be appreciated from FIG. 1 that the relationship between the D-cysteine level and the luminescent level is linear. It was confirmed that a precise determination of the D-cysteine level can be provided according to the quantitating method and the quantitating reagent of the present invention.

Accordingly, the present invention provides a method and a reagent for quantitating D-cysteine in a convenient and highly-sensitive manner. The present invention is applicable not only to D-cysteine existing in a free form in a sample but also to a D-cysteine derivative such as a D-cysteine residue in a protein derived from an organism.

The present invention is very useful in the fields of biotechnology, clinical test, medical science and the like.

All publications and patent applications cited herein are incorporated herein by reference in their entirety.

What is claimed is:

1. A method for quantitating D-cysteine, comprising the steps of:

(a) reacting D-cysteine with 2-cyano-6-hydroxybenzothiazole to produce D-luciferin; and
  (b) calculating a D-cysteine level by determining a level of luminescent generated upon reacting the produced D-luciferin with luciferase, ATP and magnesium ion.

2. A reagent for quantitating D-cysteine, which comprises 2-cyano-6-hydroxybenzothiazole, luciferase, ATP and magnesium ion.

* * * * *